United States Patent [19]

Gunn, Jr. et al.

[11] Patent Number: 5,472,958

[45] Date of Patent: Dec. 5, 1995

[54] 2-((NITRO)PHENOXYMETHYL) HETEROCYCLIC COMPOUNDS THAT ENHANCE COGNITIVE FUNCTION

[75] Inventors: David E. Gunn, Jr., Waukegan; Richard L. Elliott, Grayslake; Nan-Horng Lin, Mundelein; Hana A. Kopecka, Vernon Hills; Mark W. Holladay, Libertyville, all of Ill.

[73] Assignee: Abbott Laboratories, Abbott Park, Ill.

[21] Appl. No.: 297,454

[22] Filed: Aug. 29, 1994

[51] Int. Cl.$^6$ .......................... A61K 31/33; A61K 31/40
[52] U.S. Cl. .................. 514/210; 514/428; 548/570; 548/950
[58] Field of Search ....................... 514/210, 428

[56] References Cited

U.S. PATENT DOCUMENTS

| | | | |
|---|---|---|---|
| 3,290,212 | 12/1966 | Testa et al. | 167/55 |
| 3,577,415 | 5/1971 | Cale, jr. | 260/247.2 |
| 3,577,432 | 5/1971 | Helsley | 260/326.3 |
| 4,379,161 | 4/1983 | Thominet et al. | 424/274 |
| 4,822,778 | 4/1989 | Aberg et al. | 54/317 |
| 5,037,841 | 8/1991 | Schobe et al. | 54/373 |
| 5,130,309 | 7/1992 | Shanklin, Jr. et al. | 514/210 |
| 5,145,865 | 9/1992 | Fujii et al. | 514/424 |

OTHER PUBLICATIONS

Uhl, et al.; C.A. 92:94253j (1980), vol. 92.
Thominet et al.; C.A. 96:35075n (1982), vol. 96.

*Primary Examiner*—Joseph Paul Brust
*Attorney, Agent, or Firm*—Jerry F. Janssen; Richard A. Elder

[57] ABSTRACT

Selective and potent cholinergic ligands selective for neuronal nicotinic cholinergic channel receptors, which ligands have the formula:

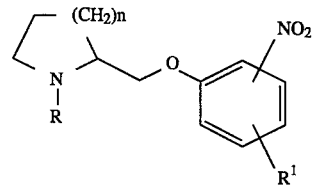

as well as pharmaceutically-acceptable salts or prodrugs thereof, which are useful in the treatment of dementias, attentional hyperactivity disorder, or substance abuse withdrawal characterized by decreased cholinergic function, one of which is also an analgesic agent, and one of which is an agent useful for treating anxiety associated with cognitive impairment.

3 Claims, No Drawings

2-((NITRO)PHENOXYMETHYL) HETEROCYCLIC COMPOUNDS THAT ENHANCE COGNITIVE FUNCTION

TECHNICAL FIELD

This invention relates to 2-((nitro)phenoxymethyl)heterocyclic compounds which are cholinergic ligands selective for neuronal nicotinic cholinergic channel receptors; to methods of preparation and pharmaceutical compositions thereof; and to uses thereof in treating cognitive, neurological and mental disorders, such as dementias and anxiety, which are characterized by decreased cholinergic function, in treating attention-deficit disorder, in treating or preventing withdrawal symptoms caused by the cessation of chronic or long term use of tobacco products, and in ameliorating the symptoms of anxiety and frustration associated with withdrawal of other addictive substances such as, for example, cocaine, diazepam or alcohol.

BACKGROUND OF THE INVENTION

Dementia is a widely-recognized and very serious health problem. Alzheimer's disease accounts for more than 50% of the dementia in the elderly, and it is also a major cause of death in Americans over age 65. Four million Americans, and 40% of those over age 85 (the fastest growing segment of the U.S. population), have Alzheimer's disease. Twenty-five percent of all patients with Parkinson's disease also suffer from a dementia similar to that seen in Alzheimer's disease. And in about 15% of patients with dementia, Alzheimer's disease and multi-infarct dementia coexist. The third most common dementia, after Alzheimer's disease and vascular dementia, is cognitive impairment due to organic brain disease related directly to alcoholism, which occurs in about 10% of alcoholics.

The precise molecular lesions causing the morphological and functional deficits associated with dementia are not known, despite intensive research efforts over the last decade. However, the most consistent abnormality for Alzheimer's disease is the degeneration of the cholinergic system arising from the basal forebrain (BF) to both the cortex and hippocampus. This is also seen in vascular dementia and cognitive impairment due to organic brain disease related to alcoholism (Bigl et al., in *Brain Cholinergic Systems*, M. Steriade and D. Biesold, eds., Oxford University Press, Oxford, 1990, pp. 364–386). In particular, decreases in markers of cholinergic neuronal function are seen in brains of patients afflicted with Alzheimer's disease (Perry et al., *Br. Med. J.*, 1978, 2:1457; Reisine et al., *Brain Res.*, 1978, 159:477; Coyle et al., *Science*, 1983, 219:1184; and McGeer et al., *Neurology*, 1984, 34:741). There are a number of other neurotransmitter systems affected by Alzheimer's disease (Davies, *Med. Res. Rev.*, 1983, 3:221). However, these are relatively less profound than the decreases in these cholinergic neuronal function markers.

Substantial reductions (30–50%) in nicotinic cholinergic channel receptors have been consistently reported in the brains of patients with Alzheimer's disease or Parkinson's disease (Kellar et al., *Brain Res.*, 1987, 436:62; and Whitehouse et al., *Neurol.*, 1988, 38:720), whereas changes in muscarinic cholinergic receptors are less remarkable and more dependent on receptor subtype.

Degeneration of the cholinergic neurotransmitter system is also seen in otherwise-healthy aged adults and rats. Decreases in cholinergic markers in the basal forebrain, decreases in cortical activities of the biosynthetic and degradative enzymes for acetylcholine, decreases in the ability to release acetylcholine from tissue slices, and decreases in numbers of cortical nicotinic cholinergic channel receptors have all been reported in such otherwise-healthy aged individuals (for a review, see Giacobini, *J. Neurosci. Res.*, 1990, 27:548). Moreover, for those cholinergic neurons that remain, aging may cause a decrease in the temporal fidelity of existing impulse flow from the basal forebrain to the cortex (Aston-Jones et al., *Brain Res.*, 1985, 325:271). These findings are consistent with pharmacological studies suggesting that cholinergic mechanisms are also, at least in part, responsible for the memory disturbances in aged animals and humans not suffering from Alzheimer's disease (Drachman and Leavitt, *Arch. Neurol.*, 1974, 30:113; and Bartus et al., *Science*, 1982, 217:408).

Other clinical symptoms that correlate with the neurodegenerative process of Alzheimer's disease include decreases in regional cerebral blood flow and cerebral glucose utilization in regions which largely parallel the areas where cholinergic deficits occur (Ingvar and Risberg, *Exp. Brain Res.*, 1962, 3:195; Ingvar et al., in *Aging: Alzheimer's Disease, Senile Dementia and Related Disorders*, Vol. 7, R. Katzman, R. D. Terry, and K. L. Bick, eds., Raven Press, 1978, p. 203; and Dastur, *J. Cerebral Blood Flow & Metabol.*, 1985, 5:1). In fact, it has been suggested that routine measurement of cerebral blood flow may be a useful procedure in evaluating patients suspected of having dementia, and of having Alzheimer's disease in particular.

Although decreases in cerebral blood flow and cerebral glucose utilization are generally reported in aged populations, it has been suggested that these decreases are secondary to other ongoing cerebral dysfunctions. Nonetheless, deficiencies in metabolic and cerebrovascular responses to pharmacologic and physiologic perturbation are consistently reported. Another recent study has shown that older rats have a smaller increase in cerebral blood flow than younger rats, in response to an electric stimulus to the basal forebrain (Linville and Americ, *Neurobiol. Aging* 1991, 12:503). Indeed, in studies that compare the degree of learning impairment to the degree of reduced cortical cerebral blood flow in aged rats a good correlation between the two is seen (Berman et al., *Neurobiol. Aging*, 1988, 9:691).

Recent clinical evidence suggests that the characteristic perfusion abnormality observed in Alzheimer's disease patients reflects regional nicotinic cholinergic deficits (Prohovnik, *Neurobiol. Aging*, 1990, 11:262). In particular, mecamylamine, a centrally-acting nicotinic receptor antagonist, reduces resting cortical perfusion in the parietotemporal cortex of humans, the area of the cortex most consistently found to be impaired in functional brain imaging of Alzheimer's disease patients. In agreement with this finding, regulation of cerebral blood flow in the frontoparietal cortex, governed by the basal forebrain, is also dependent upon nicotinic mechanisms in the rat (Americ, *J. Cerebral Blood Flow & Metabol.*, 1989, 9 (Suppl. 1): S502).

Chronic alcoholism, and more particularly the resultant organic brain disease seen in such patients, is also characterized by diffuse reductions in cortical cerebral blood flow in those brain regions where cholinergic neurons arise (basal forebrain) and to which they project (cerebral cortex) (Lofti & Meyer, *Cerebrovasc. and Brain Metab. Rev.*, 1989, 1:2). Moreover, of all the neurotransmitter systems studied, the neurotoxic effects of alcohol on the cholinergic system are thought to be the most important.

Any therapies directed towards enhancing cognitive processing should therefore be directed to maintaining a wellregulated balance between adequate cerebral blood flow, cerebral glucose utilization and cholinergic neurotransmission arising from the basal forebrain.

Pilot clinical studies suggest that nicotine may be useful for the acute treatment of deficits in attention and information processing associated with Alzheimer's disease (Sahakian et al., *Brit. J. Psych.*, 1989, 154:797; and Newhouse et al., *Psychopharmacol.*, 1988, 95:171). It has been shown that both acutely- and chronically-administered nicotine enhances cognitive function in rats (Levin et al., *Behav. Neural Biol.*, 1990, 53:269), including aged animals (Cregan et al., *Soc. Neurosci. Abstract*, 1989, 15: 2952). Additionally, anecdotal evidence suggests that people who smoke are less likely to acquire Alzheimer's disease. This is supported by animal studies that demonstrate a neuroregenerative-neuroprotective action of chronically-administered nicotine on both neuronal and vascular functions following hemitransection or MPTP-induced destruction of the nigro-striatal dopamine system (Janson et al., Prog. *Brain Res.*, 1989, 79:257; and Owman et al., *Prog. Brain Res.*, 1989, 79:267). Interestingly, in contrast to the classical down-regulation of receptors typically seen with receptor agonists, chronic nicotine administration up-regulates (50–100%) the number of receptors without affecting affinity (Benwell et al., *J. Neurochem.*, 1988, 50:1243). This effect occurs both in humans and in smaller animals such as rats (Lapchack et al., *J. Neurochem.*, 1989, 52:483).

Although various cholinergic channel agonists have been tested, both nicotine and various muscarinic agents have proven to be therapeutically sub-optimal. Nicotine has an unfavorable pharmacokinetic profile and poor oral bioavailability. The muscarinic agents, including arecoline, carbachol and RS-86, for example, also suffer from various deficiencies, such as has unfavorable pharmacokinetics in the case of arecoline, poor CNS penetration with carbachol, and poor potency and lack of selectivity for CNS receptors with RS-86. RS-86 has similar affinity for muscarinic receptors located in the heart and in cortical tissues and is a full agonist at cardiac receptors, whereas it is only a partial agonist at cortical receptors (S. B. Freedman, *Brit. J. Pharmacol.*, 1986, 87: 29P). In addition, other known cholinergic agents of the muscarinic type have many unwanted central agonist actions, including hypothermia, hypolocomotion and tremor, and serious peripheral side effects that including miosis, lacrimation, defecation and tachycardia (Benowitz et al., in *Nicotine Psychopharmacology*, S. Wonnacott, M. A. H. Russell, & I. P. Stolerman, eds., Oxford University Press, Oxford, 1990, pp. 112–157; and M. Davidson et al., in *Current Research in Alzheimer Therapy*, E. Giacobini and R. Becker, eds.; Taylor & Francis: New York, 1988; pp 333–336).

An active cholinergic agent of the nicotinic type should be able to treat a decline in cognitive ability by improving cholinergic function and cerebral blood flow. An added advantage would accrue to such a compound that was able to treat the other symptoms that accompany the earlier stages of Alzheimer's disease. One such symptom is anxiety. Anxiolytics have been used to treat the severe agitation that most Alzheimer's patients experience with the initial loss of memory (IN PHARMA, Mar. 16, 1991, pg 20). In fact, the use of anxiolytics has become an important aspect of strategies for treating Alzheimer's disease (Schmidt et al., *Drug Dev. Res.*, 1988, 14:251). Nicotine is known to have anxiolytic properties (Pomerleau et al., *Addictive Behaviors*, 1984, 9:265). It is to be expected, therefore, that nicotine or selective nicotine agonists may be useful in the treatment of the anxiety associated with dementias, such as Alzheimer's disease.

Other treatment opportunities where enhanced therapeutic benefits may be achieved by administration of nicotine or a cholinergic channel activator of the nicotinic type include attentional deficit disorder and drug withdrawal, which are accompanied by anxiety.

Attention-deficit disorder (ADD), with or without hyperactivity, is a behavioral disorder characterized by distractibility and impulsiveness. Children with this disorder cannot concentrate or control their impulsivity, especially in schooling environments. Some stimulants, for example, pemoline, have been used successfully in management of the behavioral manifestations of ADD. Nicotine is also potentially useful in treating ADD, because of its ability to improve concentration and task performance (F. T. Etscorn, U.S. Pat. No. 4,597,961, issued Jul. 1, 1986; and D. M. Warburton and K. Wesnes in *Smoking Behavior*, R. E. Thornton, ed., Churchill-Livingston, Edinburgh, 1978, pp. 19–43).

Tobacco use, especially cigarette smoking, has long been recognized as a possible cause of disease and death. Tars, carcinogens, and carbon monoxide are among the compounds in smoke that compromise the health of smokers. The most pharmacologically-active substance in tobacco products is nicotine, which is the reinforcing agent responsible for maintaining tobacco dependency (J. H. Jaffe, in *Nicotine Pharmacology: Molecular, Cellular and Behavioral Aspects*, S. Wonnacott, M. A. H. Russell and I. P. Stolerman, eds., Oxford Science Publications, Oxford, 1990, pp. 1–37).

As campaigns to encourage people to stop smoking take effect, the nicotine withdrawal syndrome associated with smoking cessation, which is characterized by craving for nicotine, irritability, frustration or anger, anxiety, difficulty in concentrating, restlessness, decreased heart rate, increase in appetite and weight gain, becomes increasingly important. It is not surprising that nicotine been found to ease the withdrawal experienced by those attempting to break tobacco dependencies. As early as 1942, Johnston reported that injections of nicotine relieved the withdrawal symptoms experienced by cigarette smokers when they stopped smoking (*Lancet*, 1942, 2:742). In recent double-blind studies, nicotine was found to be far superior to a placebo for suppressing or preventing the appearance of many of the signs and symptoms of withdrawal (J. R. Hughes et al., *Psychopharmacology*, 1984, 83:82–7; N. G. Schneider et al., *Addictive Behavior*, 1984, 9:149–56; R. J. West et al., *Journal of Addiction*, 1984, 79:215–9; K. O. Fagerstrom in *Nicotine Replacement: a Critical Evaluation*, O. F. Pomperleau and C. S. Pomperleau, eds., Alan R. Liss, Inc., New York, 1988, pp. 109–28; and J. E. Henningfield and D. R. Jasinski, ibid., pp.35–61). Irritability and impatience were reduced in at least five independent controlled studies, while anxiety and concentration difficulties were reduced in at least two studies. Other studies have shown nicotine to have been significantly more effective than a placebo in relieving depression, hunger, somatic complaints and sociability. Nicotine has also been found to be effective in reducing anger, irritability, frustration and feelings of tension, while increasing the ability to focus upon the completion of tasks, without causing general response depression, drowsiness or sedation (R. R. Hutchinson et al., U.S. Pat. No. 3,879,794, issued Mar. 11, 1975).

One approach to alleviating the symptoms of tobacco withdrawal has been to develop more efficient methods of delivering nicotine, for example, with transdermal patches (F. T. Etscorn, U.S. Pat. No. 4,597,961, issued Jul. 1, 1986).

The major problem with this approach relates to the non-selective effects of nicotine upon the heart, in particular its stimulant effects in increasing cardiac workload and oxygen demand. A selective cholinergic channel activator would be expected to be equally efficacious in relieving withdrawal symptoms, but with fewer cardiovascular liabilities.

Withdrawal from addictive substances, regardless of which particular agent is withdrawn, is in general a traumatic experience characterized by anxiety and frustration. These emotional disturbances contribute to failure in therapy and, consequently, to a return to substance dependence. Although ameliorating the feelings of anger, irritability, frustration and tension, any agent improving the individual's ability to cope and to concentrate should vastly improve the chances of successfully completing withdrawal treatment even though it would not eliminate the craving for the withdrawn drug.

It has now been discovered that compounds according to this invention are selective and potent cholinergic channel activators or ligands useful in treating these problems. Additionally, one of these compounds has been shown to have analgesic properties.

Compounds with somewhat similar structures are known.

Abreo et al. (PCT application WO 94/08992, published Apr. 28, 1994) have disclosed pyrrolidine compounds of the formula:

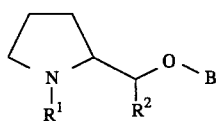

wherein $R^1$ and $R^2$ include H and $C_1$–$C_6$-alkyl, and B includes a 3-pyridinyl group further mono-substituted in a limited and specified manner with only a hydroxyl, alkyl, alkoxy, or halogen group, and have suggested these compounds as agents to enhance cognitive function.

Shanklin et al. (U.S. Pat. No. 5,130,309, issued Jul. 14, 1992) disclose 2-aryloxyalkylazetidine compounds of the formula:

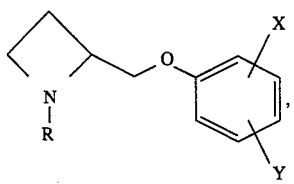

wherein R includes H and $C_1$–$C_4$-alkyl, X includes hydrogen, halogen, trifluoromethyl and $C_1$–$C_4$-alkyl, and Y is hydrogen and $C_1$–$C_4$-alkyl, and Aberg et al. (U.S. Pat. No. 4,822,778, issued Apr. 18, 1989) disclose 2-phenoxyalkylpiperidine compounds of the formula:

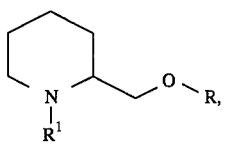

wherein $R^1$ includes hydrogen and $C_1$–$C_4$-alkyl, and R is a phenyl or cyclohexyl group optionally substituted with 1-to-4 methyl groups, each disclosing their compounds as antiarrhythmic and anticonvulsant agents.

Helsley (U.S. Pat. No. 3,577,432, issued May 4, 1971), disclosing 3-phenoxypyrrolidine compounds of the formula:

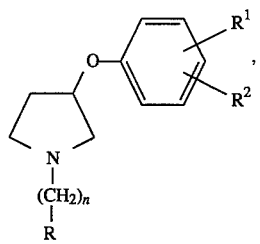

wherein R includes $C_1$–$C_4$-alkyl, and when n is 0, phenyl, and $R^1$ and $R^2$ include hydrogen, halogen, lower alkoxy, acetyl and trifluoromethyl, suggests these compounds as muscle relaxant, anti-convulsive and major tranquilizing agents. Cale (U.S. Pat. No. 3,577,415, issued May 4, 1971) discloses additional 3-phenoxypyrrolidine compounds of the formula:

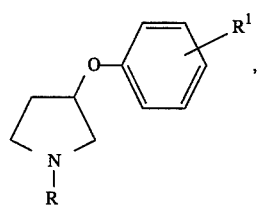

wherein R includes methyl, benzyl and carbamoyl, and $R^1$ includes carbamoyl, carboxyl, amino, aminomethyl, cyano, and acetamido, as anti-depressant agents.

Schohe et al. (U.S. Pat. No. 5,037,841, issued Aug. 6, 1991) disclose 1-substituted-3-phenoxyalkyl compounds of the formula:

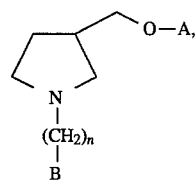

wherein A includes an optionally-substituted phenyl grouping and B includes a cyano, carboxyl, carboxyamido, sulfonamido, amino, or aminobutynyl grouping, as agents having high affinity for 5-hydroxytryptamine receptors of the 5-$HT_1$-type. Fujii et al. (U.S. Pat. No. 5,145,865, issued Sep. 8, 1992), disclosing N-phenyl-phenoxymethylpyrrolidine compounds of the formula:

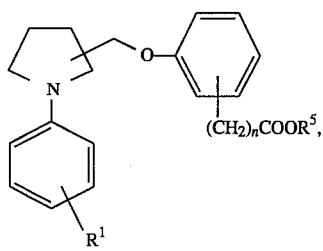

suggest that their compounds are hypolipidemic agents.

Testa et al. (U.S. Pat. No. 3,290,212, issued Dec. 6, 1966) disclose an N-methyl- 2-phenoxymethylpyrrolidine compound of the formula:

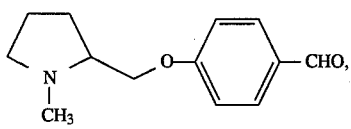

as an intermediate to larger benzamide-functionalized compounds. Then, Wander AG (published application DE 2,315, 092, October 1970), disclosing 3-phenoxymethylpyrrolidine compounds of the formula:

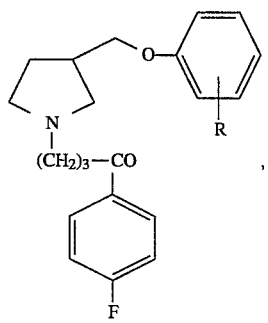

proposed its compounds as antipsychotic or muscle relaxant agents.

We have found that the novel 2-((nitro)phenoxymethyl-)heterocyclic compounds of the present invention possess unexpected utility as cholinergic channel activators or ligands of the nicotinic type. These compounds are therefore useful in treating cognitive, neurological and mental disorders characterized by decreased cholinergic function, such as, for example, attention-deficit disorder, dementias, and anxiety associated with cognitive impairment and substance abuse withdrawal.

Nothing in the referenced prior art discloses or suggests that the novel compounds of the present invention would possess these activities. Furthermore, the cited references neither disclose nor suggest that a nitro-substituted analog of the inventions thereof would have any activity, including in the biological models utilized to estimate the clinical utilities of their novel compounds.

SUMMARY OF THE INVENTION

The present invention is directed to novel 2-((nitro)phenoxymethyl)heterocyclic compounds of the formula (I):

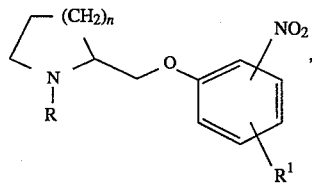

and pharmaceutically-acceptable salts or prodrugs thereof, wherein n, R and $R^1$ are specifically defined; to pharmaceutical compositions comprising a therapeutically-effective amount of these compounds and a pharmaceutically-acceptable carrier or diluent; and to a method of treating cognitive, neurological and mental disorders characterized by decreased cholinergic function, such as, for example, attention-deficit disorder, dementias, and anxiety associated with cognitive impairment and substance abuse withdrawal, as well as to a method for treating pain.

DETAILED DESCRIPTION OF THE INVENTION

The novel compounds of the present invention are heterocyclic compounds substituted at the 1-position with a hydrogen or methyl group and at the 2-position with a nitrophenoxymethyl group, as represented by formula (I):

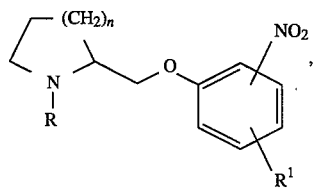

wherein n is 0 or 1, R is hydrogen or methyl, and $R^1$ is hydrogen or nitro; or a pharmaceutically-acceptable salt or prodrug thereof.

The following are representative of the novel compounds of the present invention:
2(S)-(3-(nitro)phenoxymethyl)pyrrolidine;
1-methyl-2(S)-(3-(nitro)phenoxymethyl)pyrrolidine;
2(R)-(3-(nitro)phenoxymethyl)pyrrolidine;
1-methyl-2(R)-(3-(nitro)phenoxymethyl)pyrrolidine;
2(S)-(3-(nitro)phenoxymethyl)azetidine; and
1-methyl-2(R)-(3-(nitro)phenoxymethyl)azetidine.

The present invention is also directed to pharmaceutical compositions comprising a therapeutically-effective amount of a compound of formula (I) and a pharmaceutically-acceptable carrier or diluent.

In another aspect of the present invention is provided a method of treating cognitive, neurological and mental disorders, which are characterized by decreased cholinergic function in humans and lower mammals, by administration to a patient in need of such treatment of a compound of formula (I).

In another aspect of the present invention is provided a method of treating cognitive, neurological and mental disorders, characterized by decreased cholinergic function in humans and lower mammals, by administration to such mammals of a compound selected from the group consisting of:
2(S)-(3-fluorophenoxymethyl)pyrrolidine;
2(S)-(3-fluorophenoxymethyl)-1-methylpyrrolidine;
2(S)-(3,5-difluorophenoxymethyl)pyrrolidine;
2(S)-(3,5-difluorophenoxymethyl)-1-methylpyrrolidine;

2(R)-(3-fluorophenoxymethyl)pyrrolidine;
2(R)-(3-fluorophenoxymethyl)-1-methylpyrrolidine;
2(S)-(2,3-difluorophenoxymethyl)pyrrolidine;
2(S)-(2,3-difluorophenoxymethyl)-1-methylpyrrolidine;
2(S)-(3,4-difluorophenoxymethyl)pyrrolidine;
2(S)-(3,4-difluorophenoxymethyl)-1-methylpyrrolidine;
2(S)-(3-chlorophenoxymethyl)-1-methylpyrrolidine;
2(S)-(3,4-dichlorophenoxymethyl)-1-methylpyrrolidine;
2(S)-(3-(acetamido)phenoxymethyl)pyrrolidine;
2(S)-(3-cyanophenoxymethyl)pyrrolidine;
2(S)-(3-cyanophenoxymethyl)-1-methylpyrrolidine;
1-methyl-2(S)-(phenoxymethyl)pyrrolidine; and
2(S)-(phenoxymethyl)pyrrolidine.

In yet another aspect of the present invention is provided a method of treating pain by administration of (R)-2-(3-(nitro)phenoxymethyl)pyrrolidine or a pharmaceutically-acceptable salt or prodrug thereof.

The term, "prodrug", refers to compounds that are rapidly transformed in vivo to yield the parent compounds of Formula (I), as for example, by hydrolysis in blood. T. Higuchi and V. Stella provide a thorough discussion of the prodrug concept in *Prodrugs as Novel Delivery Systems*, Vol. 14 of the A.C.S. Symposium Series, American Chemical Society (1975). Examples of esters useful as prodrugs for compounds containing carboxyl groups may be found on pages 14–21 of *Bioreversible Carriers in Drug Design: Theory and Application*, edited by E. B. Roche, Pergamon Press (1987).

The term, "prodrug ester group", refers to any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art.

The term, "administration", of the cholinergic agent or composition, as used herein, refers to systemic use as when taken orally, parenterally, by inhalation spray, by nasal, rectal or buccal routes, or topically as ointments, pastes, creams, lotions, gels, powders, solutions, sprays, inhalants or transdermal patches in dosage form unit formulations containing conventional nontoxic pharmaceutically-acceptable carriers, adjuvants and vehicles as desired.

The term, "parenteral", as used herein, includes intravenous, intramuscular, intraperitoneal, intrasternal, subcutaneous and intraarticular injection as well as via infusion techniques.

By "pharmaceutically-acceptable", it is meant those salts, amides and esters which are, within the scope of sound medical judgment, suitable for use in contact with the tissues of humans and animals without undue toxicity, irritation, allergic response and the like, and are commensurate with a reasonable benefit/risk ratio, effective for their intended use in the treatment of psychological, neurological, cardiovascular and addictive behavior disorders. Pharmaceutically-acceptable salts are well known in the art. For example, S. M. Berge, et al. describe pharmaceutically-acceptable salts in detail in *J. Pharmaceutical Sciences,* 1977, 66:1–19. The salts may be prepared in situ during the final isolation and purification of the compounds of Formula (I), or separately by reacting the free base function with a suitable organic acid. Representative acid addition salts include hydrochloride, hydrobromide, sulfate, bisulfate, acetate, oxalate, valerate, oleate, palmitate, stearate, laurate, borate, benzoate, lactate, phosphate, toluenesulfonate, methanesulfonate, citrate, maleate, fumarate, succinate, tartrate, ascorbate, glucoheptonate, lactobionate, lauryl sulfate salts and the like. Representative alkali or alkaline earth metal salts include sodium, calcium, potassium, magnesium salts and the like. Examples of pharmaceutically-acceptable, nontoxic amides of the compounds of Formula I include amides derived from $C_1$–$C_6$-alkyl carboxylic acids wherein the alkyl groups are straight- or branched-chain, aromatic carboxylic acids such as derivatives of benzoic acid and heterocyclic carboxylic acids, including furan-2-carboxylic acid or nicotinic acid. Amides of the compounds of Formula I may be prepared according to conventional methods and include amino acid and polypeptide derivatives of the amines of Formula I.

As used herein, the term, "pharmaceutically-acceptable carriers", means a non-toxic, inert solid, semi-solid or liquid filler, diluent, encapsulating material or formulation auxiliary of any type. Some examples of the materials that may serve as pharmaceutically-acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants may also be present in the composition, according to the judgment of the formulator. Examples of pharmaceutically-acceptable antioxidants include water-soluble antioxidants, such as ascorbic acid, cysteine hydrochloride, sodium bisulfite, sodium metabisulfite, sodium sulfite, and the like; oil-soluble antioxidants, such as ascorbyl palmitate, butylated hydroxyanisole (BHA), butylated hydroxytoluene (BHT), lecithin, propyl gallate, alpha-tocopherol and the like; and the metal chelating agents such as citric acid, ethylenediamine tetraacetic acid (EDTA), sorbitol, tartaric acid, phosphoric acid and the like.

By a "therapeutically-effective amount" of the cholinergic channel ligand agent, is meant a sufficient amount of the compound to treat cholinergically-related disorders at a reasonable benefit/risk ratio applicable to obtain a desired therapeutic response. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidentally with the specific compound employed; and like factors well known in the medical arts. Total daily dose of the compounds of this invention administered to a host in single or divided doses may be in amounts as determined by the attending physician, typically, for example, in amounts of from about 0.001 to 100 mg/kg body weight daily and preferably 0.01 to 10 mg/kg/day. Dosage unit compositions may contain such amounts of submultiples thereof to make up the daily dose.

The present invention includes one or more of the compounds of formula (I) prepared and formulated with one or more non-toxic pharmaceutically-acceptable compositions, as described below.

Compositions suitable for parenteral injection may comprise pharmaceutically-acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

If desired, and for more effective distribution, the compounds may be incorporated into slow-release or targeted-delivery systems, such as polymer matrices, liposomes, and microspheres. They may be sterilized, for example, by filtration through a bacteria-retaining filter, or by incorporating sterilizing agents in the form of sterile solid compositions, which may be dissolved in sterile water, or some other sterile injectable medium immediately before use.

Solid dosage forms for oral administration may include capsules, tablets, pills, powders, and granules. In such solid dosage forms, the active compound is admixed with at least one inert customary excipient (or carrier), such as sodium citrate or dicalcium phosphate, and additionally (a) fillers or extenders, as for example, starches, lactose, sucrose, glucose, mannitol and silicic acid; (b) binders, as for example, carboxymethylcellulose, alginates, gelatin, polyvinylpyrrolidone, sucrose and acacia; (c) humectants, as for example, glycerol; (d) disintegrating agents, as for example, agar-agar, calcium carbonate, potato or tapioca starch, alginic acid, certain complex silicates and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules, using such excipients as lactose or milk sugar, as well as high molecular weight polyethylene glycols, and the like.

Solid dosage forms such as tablets, dragees, capsules, pills and granules may be prepared with coatings and shells, such as enteric coatings and others well known in this art. They may contain pacifying agents, and may also be of such composition that they release the active compound or compounds in a certain part of the intestinal tract in a delayed manner. Examples of embedding compositions which may be used are polymeric substances and waxes.

The active compounds may also be in micro-encapsulated form, if appropriate, with one or more of the above-mentioned excipients.

Liquid dosage forms for oral administration include pharmaceutically-acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, these liquid dosage forms may also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal or vaginal administrations are preferably suppositories which can be prepared by mixing the compounds of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical or transdermal administration of a compound of this invention further include ointments, pastes, creams, lotions, gels, powders, solutions, sprays, inhalants or transdermal patches. Transdermal administration via a transdermal patch is a particularly effective and preferred dosage form of the present invention. The active component is admixed under sterile conditions with a pharmaceutically-acceptable carrier and any needed preservative, buffers or propellants as may be required. It is known that some agents may require special handling in the preparation of transdermal patch formulations. For example, compounds that are volatile in nature may require admixture with special formulating agents or with special packaging materials to assure proper dosage delivery. In addition, compounds which are very rapidly absorbed through the skin may require formulation with absorption-retarding agents or barriers. Ophthalmic formulations, eye ointments, powders and solutions are also contemplated as being within the scope of this invention.

The present compounds may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes may be used. The present compositions in liposome form may contain, in addition to the compounds of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y., (1976), p 33 et seq.

In order to reduce unwanted peripherally-mediated side-effects, it is advantageous, but not essential, to incorporate into the composition a peripherally-acting anti-cholinergic such as N-methylscopolamine, N-methylatropine, propantheline, methantheline, or glycopyrrolate.

Compounds of the invention which have one or more asymmetric carbon atoms may exist as the optically-pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof. The terms "R" and "S" used herein are configurations as defined in *IUPAC 1974 Recommendations for Section E, Fundamental Stereochemistry*, Pure Appl. Chem., 1976, 45:13–30.

The compounds of the present invention may be synthesized as shown in reaction Scheme I presented below using the reactions and techniques described in this section. The reactions are performed in a solvent appropriate to the reagents and materials employed are suitable for the transformation being effected. It is understood by those skilled in the art of organic synthesis that the functionality present on the heterocyclic ring and other portions of the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to skilled practitioners in the art. The use of nitrogen-protecting groups is well known in the art for protecting amino groups against undesirable reactions during a synthetic procedure and many such protecting groups are known, cf., for example, T. H. Greene and P. G. M. Wuts, *Protective Groups in Organic Synthesis*, 2nd edition, John Wiley & Sons, New York (1991).

ABBREVIATIONS

The following abbreviations are used throughout this application: BOC for t-butyloxycarbonyl; $CDCl_3$ for deuterochloroform; $D_2O$ for deuterium oxide, DEAD for diethyazodicarboxylate; DMSO-$d_6$ for deuterodimethylsulfoxide; TBAD for di-t-butyl azodicarboxylate; TFA for trifluoroacetic acid; THF for tetrahydrofuran; tlc for thin-layer chromatography; TPP for triphenylphosphine;

SCHEME

The compounds of the present invention are prepared in accordance with Scheme 1 below, wherein a BOC-protected prolinol (1) is the starting material. This compound (1) may be obtained commercially or may be prepared by standard methods known to those skilled in the art, from the appropriate D- or L-proline, by first protecting the nitrogen with the BOC group by reaction of proline with di-t-butyl dicarbonate, followed by reduction of the carboxyl group to the alcohol, by reduction with any acceptable reducing agent, such as, for example, sodium borohydride/$I_2$ or $BH_3$.THF, in a suitable solvent and under appropriate reaction conditions as may be set by a skilled chemist.

Compound (1) is reacted with the appropriately substituted phenol of formula (2), wherein $R^1$ and $R^2$ are as described above, that are generally available commercially or easily prepared under standard synthetic conditions known to those skilled in the art, under Mitsunobu reaction conditions (a trialkyl- or triarylphosphine and a dialkylazodicarboxylate in a suitable solvent), to give the BOC-protected intermediate of formula (3). By removing the BOC group with HCl or TFA, the compound (4) is prepared, which is the compound of formula (I) above, wherein R is hydrogen. By reacting the compound (3) with a reducing compound under the proper conditions, such as formic acid and formalin at temperatures higher than 70° C., the compound (5) is prepared, which is the compound of formula (I) above, wherein R is methyl.

Scheme 1

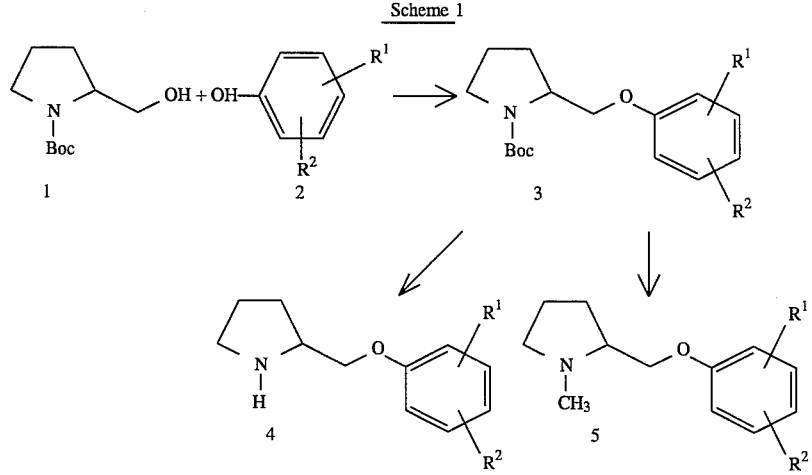

IN VITRO DETERMINATION Of NEURONAL NICOTINIO RECEPTOR BINDING POTENCIES AND SELECTIVITY

For the purpose of identifying compounds as cholinergic agents which are capable of interacting with cholinergic channel receptors in the brain, a ligand-receptor binding assay was carried out as the initial screen. Compounds of the present invention were effective at interacting with neuronal nicotinic cholinergic receptors as assayed for their ability (compared to (−)-nicotine) to displace radioligand from neuronal nicotinic cholinergic channel receptors labeled with [$^3$H]-cytisine ([$^3$H]-CYT).

The ability of the compounds of the invention to interact with cholinergic channel receptors can be demonstrated in vitro using the following protocol.

Protocol For Determination of Nicotinic Cholinergic Channel Receptor Binding Potencies of Ligands Binding of [$^3$H]-cytisine ([$^3$H]-CYT) to nicotinic receptors was accomplished using crude synaptic membrane preparations from whole rat brain (Pabreza et al., *Molecular Pharmacol.*, 1990, 39:9). Washed membranes were stored at −80° C. prior to use. Frozen aliquots were slowly thawed and resuspended in 20 volumes of buffer (containing: 120 mM NaCl, 5 mM KCl, 2 mM MgCl$_2$, 2 mM CaCl$_2$ and 50 mM Tris-Cl, pH 7.4 @4° C.). After centrifuging at 20,000×g for 15 minutes, the pellets were resuspended in 30 volumes of buffer. Homogenate (containing 125–150 µg protein) was added to triplicate tubes containing concentrations of test compound and [$^3$H]-CYT (1.25 nM) in a final volume of 500 µL. Samples were incubated for 60 minutes at 4° C., then rapidly filtered through Whatman GF/B filters presoaked in 0.5% polyethylimine using 3×4 mL of ice-cold buffer. The filters are counted in 4 mL of Ecolume® (ICN). Nonspecific binding was determined in the presence of 10 µM (−)-nicotine and values were expressed as a percentage of total binding. IC$_{50}$ values were determined with the RS-1 (BBN) nonlinear least squares curve-fitting program and IC$_{50}$ values were converted to Ki values using the Cheng and Prusoff correction (Ki=IC$_{50}$/(1+[ligand]/Kd of ligand). Alternately, data were expressed as a percentage of the total specific binding. The results (shown in Table 1) suggest that the compounds of the present invention have high affinity for the neuronal nicotinic cholinergic channel receptor.

TABLE 1

Binding to Neuronal Nicotinic Receptors

| Example number | Ki (nM) |
|---|---|
| (−)-nicotine | 0.69 |
| 1 | 2.9 |
| 2 | 9.0 |
| 3 | 2.5 |
| 4 | 132 |
| 5 | 17.2 |
| 6 | 5.1 |
| 7 | 22.3 |
| 8 | 15.7 |
| 9 | 11.6 |
| 10 | 90.7 |
| 11 | 74.3 |
| 12 | 81.4 |
| 13 | 17.5 |
| 14 | 18.0 |
| 15 | 37.7 |
| 16 | 112 |
| 17 | 142 |
| 18 | 18 |
| 19 | 64 |
| 20 | 42.5 |
| 21 | 108 |
| 22 | 6.8 |
| 23 | 29 |

Analgesia testing

Analgesia was measured using an automated hot-plate analgesia monitor (model #AHP16AN, Omnitech Electronics, Inc., Columbus, Ohio). The temperature of the hot-plate was maintained at 55° C. Male CD-1 mice (Charles River, Portage, Mich.) weighing 30 to 35 g were used for all testing. Mice were placed on the hot-plate and the latency to jump (i.e., first 10 jumps) was recorded. Mice were removed from the apparatus either after ten jumps were made or a maximally-allowed time of 240 sec elapsed, whichever occurred first. The design of the apparatus allowed for testing of several animals (e.g., 8) at once. The latency (sec) until the tenth jump was used for statistical analysis. Data (Table 2) were statistically evaluated with ANOVA (Stat-View II™ program, Abacus Concepts, Inc., Berkeley, Calif.) and compared to the reference standard analgesic morphine.

TABLE 2

Results of Analgesia Testing

| Compound. | Dose range tested | Effective doses* (µmol/kg) | Percent change from saline |
|---|---|---|---|
| Morphine | 3–12 | 3, 6, 12§ | 257 (at 12) |
| Example 3 | 6.2–190 | 6.2, 19§, 62 | 60.7 (at 19) |

*Doses for which a statistically significant effect was observed. § = best dose.

Elevated Plus-Maze Studies in Mouse and Rat

The elevated plus-maze is a conflict test that probes anxiolytic activity of test compounds (Lister, *Psychopharmacology*, 1987, 92:180). It is based on the fact that exposure of an animal to an elevated open arm leads to an avoidance response considerably stronger than that evoked by exposure to an enclosed arm.

The apparatus required to perform this test in mice is made of plywood and consists of two open arms (17×8 cm) and two enclosed arms (17×8×15 cm) extending from a central platform (8×8 cm). It is mounted on a plywood base rising 39 cm above the floor. Mice are released on the central platform and the time spent in the open and enclosed arms is recorded during a 5 minute test period. The test compounds were administered to CD1 mice 15 minutes before the test. (−)Nicotine (0.62 and 1.9 µmol/kg, p<0.05) induced a significant increase in the time spent by the mice in the open arms of the maze (a measure of anxiolytic effect) as compared to saline-injected mice.

The same protocol was applied in rats (male Wistar strain), but a larger maze was used (open arms 50×10 cm, enclosed arms 50×10×40 cm) raised 50 cm above the floor.

The results of the experimental compounds upon the the time spent by the animals in the open arms of the maze are given in Table 3. The data in Table 3 demonstate the utility of these compounds as anxiolytic agents.

TABLE 3

Results of In Vivo Tests for Elevated Plus-Maze (EPM)*

| Example # | Mouse EPM (µmol/kg) | Rat EPM (µmol/kg) |
|---|---|---|
| (−)-nicotine | significant [0.19–0.62] | significant [1.9] |
| 1 | significant [0.62–1.9] | significant [0.19, 6.2] |

*Results are expressed in levels of improvement in performance at the dose range tested.

The following examples, which are provided for illustration and not limitation of the invention, will serve to further illustrate preparation of the novel compounds of the inven-

EXAMPLE 1

2(S)-(3-(Nitro)phenoxymethyl)pyrrolidine hydrochloride 1a. (S)-1-t-BOC-2-pyrrolidinemethanol N-t-BOC-L-proline (Sigma Chemical Co., 12.97 g, 60.02 mmol) was dissolved in anhydrous THF and brought to 0° C. with stirring. Borane/THF complex was added dropwise via syringe over a 10 minute period. The reaction mixture was stirred at room temperature for 1 hour, then the reaction was quenched slowly with saturated $NaHCO_3$ and stirred for an additional hour. The solvent was removed in vacuo, and the residue was diluted with $H_2O$. The desired compound was extracted from the aqueous phase with $Et_2O$ (3×). The organic layer was then washed with brine (2×) dried ($MgSO_4$) and evaporated. The resulting material was carried on without further purification.

1b. (S)-1-t-Butoxycarbonyl-2-(3-(nitro)phenoxymethyl)pyrrolidine

To 100 mL of THF cooled to 0° C. was added 1.3 g (5.6 mmol) of triphenylphosphine (TPP) (Aldrich) and 1.5 g (5.6 mmol) of diethyl azodicarboxylate (DEAD) (Aldrich), and the reaction was stirred for 0.5 hr. A 750 mg (3.73 mmol) sample of (S)-1-tobutoxycarbonyl-2-pyrrolidinemethanol (from step 1a above) and 779 mg (5.6 mmol) of 3-nitrophenol (Aldrich) were added to the complex of TPP and DEAD in 30 mL of THF. The reaction was stirred for 40 hr, the solvents were removed under vacuum, and the residue was chromatographed on silica gel, eluting with 1:1 chloroform:hexane to give 490 mg of the title compound.

1c. 2(S)-(3-(Nitro)phenoxymethyl)pyrrolidine hydrochloride

A 159 mg sample of the BOC-protected intermediate from step 1b above was dissolved in 10 mL of 1:1 TFA/methylene chloride and stirred at room temperature for 16 hr. The solvents were removed by evaporation, and excess 10% aqueous $NaHCO_3$ was added. The solution was extracted 3× with methylene chloride, the extract was dried over $MgSO_4$ and the solvent was removed. The residue was purified by column chromatography on silica gel, eluting with 10:1 chloroform:methanol. The product was dissolved in ether and treated with HCl/ether. The white precipitate was filtered off, washed with ether, and dried under vacuum to afford 71 mg of the title product. MS: 223 $(M+H)^+$, 240 $(M+NH_4)^+$. NMR ($D_2O$) δ: 1.91–2.36 (m, 4H), 3.39–3.46 (m, 2H), 4.14 (dq, 1H, J=3.3, 8 Hz), 4.27 (dd, 1H, J=7.7, 10.6 Hz), 4.50 (dd, 1H, J=3.3, 10.6 Hz), 7.42–7.46 (m, 1H), 7.59 (t, 1H, 8 Hz), 7.87 (t, 1H, 2.5), 7.95 (ddd, 1H, J= 1, 2, 3.3 Hz). Anal. Calcd for $C_{11}H_{15}ClN_2O_3$: C, 51.07; H, 5.84; N, 10.83; Found: C, 51.01; H, 5.88; N, 10.63.

EXAMPLE 2

1-Methyl-2(S)-(3-(nitro)phenoxymethyl)pyrrolidine hydrochloride

A 500 mg (1.12 mmol) sample of (S)-1-t-Butoxycarbonyl-2-(3 -(nitro)phenoxymethyl)pyrrolidine, from Example 1b above, was dissolved in 18 mL of a 1:2 mixture of formic acid:formaldehyde, and stirred for 5 hr at 70° C. The reaction was stopped by addition of water, and the mixture was extracted 3×10 mL with chloroform. The aqueous layer was adjusted to pH 12 with $K_2CO_3$ and then extracted with chloroform. The solvent was dried over $MgSO_4$ and removed under vacuum to yield the crude product, which was then chromatographed on silica gel, to give 302 mg. The title compound was then prepared according to the procedure described in Example 1c. MS: 237 $(M+H)^+$, 254 $(M+NH_4)^+$. NMR ($D_2O$) δ: 2.07–2.26 (m, 3H), 2.39–2.46 (m, 1H), 3.05 (s, 3H), 3.28 (br s, 1H), 3.76 (br s, 1H), 3.95 (br s, 1H), 4.38 (dd, 1H, J=6.3, 12.4), 4.55 (dd, 1H, J=2.6, 11.4 Hz), 7.45 (dd, 1H, J=2.6, 8.4 Hz), 7.60 (t, 1H, J=8 Hz), 7.89 (t, 1H, J=2.2 Hz), 7.95 (m, 1H). Anal. Calcd for $C_{12}H_{17}ClN_2O_3$: C, 52.85; H, 6.28; N, 10.27; Found: C, 52.65; H, 6.19; N, 10.12.

EXAMPLE 3

2(R)-(3-(nitro)phenoxymethyl)pyrrolidine hydrochloride 3a. (R)-1-t-Butoxycarbonyl-2-(3-(nitro)phenoxymethyl)pyrrolidine A 1.5 g (7.46 mmol) sample of (R)-1-t-butoxycarbonyl-2-pyrrolidinemethanol (prepared as in Example 1b above, except starting with the N-BOC-D-proline (Sigma) instead of the N-BOC-L-proline) and 1.56 g (11.19 mmol) of 3-nitrophenol (Aldrich) were added to a complex of TPP and DEAD (prepared as in Example 1 above, 11.2 mmol of each) in 50 mL of THF. The reaction was stirred for 16 hr, the solvents were removed under vacuum, and the residue was chromatographed on silica gel, eluting with 1:1 chloroform:hexane to give 670 mg of the title compound.

3b. 2(R)-(3-(Nitro)phenoxymethyl)pyrrolidine hydrochloride

A 300 mg sample of the purified product from step 3a above was treated according to the procedure of Example 1c to afford 79 mg of the title product. MS: 223 $(M+H)^+$, 240 $(M+NH_4)^+$. NMR ($D_2O$) δ: 1.91–2.36 (m, 4H), 3.41–3.45 (t, 2H, J=7 Hz), 4.14 (dq, 1H, J=4, 8 Hz), 4.27 (dd, 1H, J=7.7, 10.6 Hz), 4.50 (dd, 1H, J=3.3, 10.6 Hz), 7.42–7.45 (m, 1H), 7.59 (t, 1H, 8 Hz), 7.87 (t, 1H, 2.4), 7.92–7.96 (m, 1H). Anal. Calcd for $C_{11}H_{15}ClN_2O_3$: C, 51.07; H, 5.84; N, 10.83; Found: C, 50.83; H, 5.82; N, 10.70.

EXAMPLE 4

(R)-1-Methyl-2-(3-(nitro)phenoxymethyl)pyrrolidine

A 300 mg (10.67 mmol) sample of (R)-1-t-butoxycarbonyl-2-(3 -(nitro)phenoxymethyl)-pyrrolidine, from Example 3a above, was dissolved in 15 mL of a 1:2 mixture of formic acid:formaldehyde, and stirred for 16 hr at 67° C. The reaction was stopped by addition of water, and the mixture was extracted 3× 10 mL with chloroform. The aqueous layer was adjusted to pH 12 with $K_2CO_3$ and then extracted with chloroform. The solvent was dried over $MgSO_4$ and removed under vacuum to yield the crude product, which was then chromatographed on silica gel, to give 201 mg. The title compound was then prepared according to the procedure described in Example 1c. MS: 237 $(M+H)^+$, 254 $(M+NH_4)^+$. NMR ($D_2O$) δ: 2.07–2.26 (m, 3H), 2.38–2.46 (m, 1H), 3.05 (s, 3H), 3.22–3.34 (m, 1H), 3.76 (brs, 1H), 3.95 (br s, 1H), 4.38 (dd, 1H, J=6,12.), 4.55 (dd, 1H, J=3, 11 Hz), 7.45 (m, 1H), 7.60 (t, 1H, J=8 Hz), 7.89 (t, 1H, J=2.2 Hz), 7.95 (m, 1H). Anal. Calcd for $C_{12}H_{17}ClN_2O_3$: C, 52.85; H, 6.28; N, 10.27; Found: C, 52.61;H, 6.29; N, 10.04.

EXAMPLE 5

2(S)-(3-Fluorophenoxymethyl)-pyrrolidine hydrochloride 5a. (S)-1-t-BOC-2-pyrrolidinemethanol N-t-BOC-L-proline (Sigma Chemical Co., 12.97 g, 60.02 mmol) was dissolved in anhydrous THF and brought to 0° C. with stirring. Borane/THF complex was added dropwise via syringe over a 10 minute period. The reaction mixture was stirred at room temperature for 1 hour, then the reaction was quenched slowly with saturated NaHCO$_3$ and stirred for an additional hour. The solvent was removed in vacuo, and the residue was diluted with H$_2$O. The desired compound was extracted from the aqueous phase with Et$_2$O (3×). The organic layer was then washed with brine (2×) dried (MgSO$_4$) and evaporated. The resulting material was carried on without further purification.

5b. (S)-N-BOC-2-(3-fluorophenoxymethyl)-pyrrolidine

To 100 mL of THF cooled to 0° C. was added 5.9 g (22.4 mmol) of triphenylphosphine (TPP) (Aldrich) and 5.2 g (22.4 mmol) of di-t-butyl azodicarboxylate (TBAD) (Aldrich), and the reaction was stirred for 0.5 hr. To this solution was added 3.0 g (14.9 mmol) of the (S)-1-t-BOC-2-pyrrolidinemethanol, from step 5a above, and 2.5 g (22.4 mmol) of 3-fluorophenol (Aldrich). The reaction mixture was stirred at room temperature for 48 hr. The THF was removed by evaporation, and EtOAc/CHCl3/hexanes was added, and the precipitated triphenylphosphine oxide by-product removed by filtration. The filtrate was concentrated then chromatographed over silica gel, eluting with 2% CHCl$_3$ in hexane, then 50% CHCl$_3$ in hexane, to afford the product (1.5 g).

5c. 2(S)-(3-Fluorophenoxymethyl)-pyrrolidine hydrochloride

A 200 mg (0.68 mmol) sample of the BOC-protected intermediate from step 1a above was dissolved in 10 mL of 1:1 TFA/methylene chloride and stirred at room temperature for 16 hr. The solvents were removed by evaporation, and excess 10% aqueous HCl was added. The solution was extracted 3× with methylene chloride, the extract was dried over MgSO$_4$ and the solvent was removed. The residue was dissolved in ether and triturated with HCl/ether. The white precipitate was filtered off, washed with ether, and dried under vacuum to yield 28 mg of the title compound. MS: 196 (M+H)$^+$, 213 (M+NH$_4$)$^+$. NMR (D$_2$O) δ: 1.90–2.34 (m, 4H), 3.43 (dt, 2H), J=1, 6 Hz), 4.05–4.20 (m, 2H), 4.16 (dd, 1H, J=3, 10 Hz), 6.81–6.87 (m, 3H), 7.33–7.42 (m, 1H). Anal. Calcd for C$_{12}$H$_{16}$ClFNO.0.25 H$_2$O: C, 57.86; H, 6.76; N, 5.59; Found: C, 57.60; H, 6.65; N, 5.59.

EXAMPLE 6

2(S)-(3-Fluorophenoxymethyl)-1-methyl-pyrrolidine hydrochloride

To 100 mL of THF cooled to 0° C. was added 6.9 g (230.3 mmol) of triphenylphosphine (TPP) (Aldrich) and 8.1 g (262.3 mmol) of di-t-butyl azodicarboxylate (TBAD) (Aldrich), and the reaction was stirred for 0.5 hr. To this solution was added 2.3 g (115.2 mmol) of (S)-1-methyl-2-pyrrolidinemethanol (Aldrich) and 4.4 g (112.1 mmol) of 3-fluorophenol (Aldrich), and the reaction was stirred for 16 hr, allowing the temperature to rise to room temperature. The THF was removed by evaporation, 15% HCl and methylene chloride were added. The aqueous layer was adjusted to approx. pH 12 with solid K$_2$CO$_3$, then extracted 3× with methylene chloride. The extracts were combined, dried and evaporated. The residue was purified by flash chromatography, eluting with 50:50:2:1 (EtOAc/CH$_2$Cl$_2$/EtOH/NH$_4$OH) The solvent was removed, the residue dried under vacuum, and the residue dissolved in ether. HCl in ether was added slowly, with trituration, followed by removal of the solvent and drying to give 0.32 g of the title compound. MS: 210 (M+H)$^+$, 227 (M+NH$_4$)$^+$. NMR (D$_2$O) δ: 2.01–2.24 (m, 3H), 2.34–2.43 (m, 1H), 3.13–3.27 (m, 1H), 3.03 (s, 3H), 3.13–3.27 (m, 1H), 3.74–3.79 (m, 1H), 3.89–3.91 (m, 1H), 4.27 (dd, 1H, J=11, 3.3 Hz), 4.45 (dd, 1H, J=11.3.3 Hz), 6.82–6.89 (m, 3H), 7.34–7.43 (m, 1H). Anal. Calcd for C$_{12}$H$_{16}$FNO.HCl: C, 58.65; H, 6.97; N, 5.70; Found: C, 58.25; H, 6.84; N, 5.57.

EXAMPLE 7

2(S)-(3,5-Difluorophenoxymethyl)pyrrolidine hydrochloride 7a. (S)-N-BOC-2-(3,5-difluorophenoxymethyl)-pyrrolidine A complex (38.5 mmol) between TPP and TBAD in 100 mL of THF was prepared as described in Example 5b above. To this solution was added 5.15 g (25.6 mmol) of the (S)-1-t-BOC-2-pyrrolidinemethanol, from Example 1a above, and 5 g (38.5 mmol) of 3,5-difluorophenol (Aldrich). The reaction mixture was stirred at room temperature for 16 hr. The THF was removed by evaporation, and 15% HCl and methylene chloride were added. The aqueous layer was adjusted to approx. pH 12 with solid K$_2$CO$_3$, then extracted 333 with methylene chloride. The extracts were combined, dried and evaporated. The residue was crystallized from hexane, then chromatographed over silica gel, eluting with 5–7% CHCl$_3$ in hexane.

7b. (S)-2-(3,5-Difluorophenoxymethyl)-pyrrolidine hydrochloride

A 0.26 g (0.83 mmol) sample of the BOC-protected compound from step 7a was dissolved in 10 mL of 1:1 CH$_2$Cl$_2$:TFA and stirred at room temperature until tlc showed no starting material. The solvent and reagent were removed by evaporation. The residue was suspended in 10% aqueous HCl, which was then adjusted to pH 12 with K$_2$CO$_3$, and the mixture was extracted with methylene chloride. The solvent was removed, and the residue was dried, then suspended in ether. Addition of ether/HCl precipitated the title product, which was wash with ether and dried to yield 0.62 g of the title compound. MS: 214(M+H)$^+$, 231 (M+NH$_4$)$^+$, 248 (M+NH$_4$NH3)$^+$. NMR (D$_2$O) δ: 1.87–2.33 (m, 4H), 3.41 (t, 2H, J=7), 4.05–4.12 (m, 2H), 4.38 (dd, 1H), 6.62–6.71 (m, 3H). Anal. Calcd for C$_{11}$H$_{14}$ClF$_2$NO.0.45 H$_2$O: C, 51.25; H, 5.82; N 5.43; Found: C, 51.36; H, 5.35; N, 5.45.

EXAMPLE 8

2(S)-(3,5-Difluorophenoxymethyl)-1-methyl-pyrrolidine hydrochloride

A 0.25 g (0.8 mmol) sample of (S)-N-BOC-2-(3,5-difluorophenoxymethyl)pyrrolidine, from Example 7b above, was dissolved in 10 mL of a 2:1 mixture of formic acid:formaldehyde and stirred for 16 hr at reflux. To this solution was added excess 10% HCl, and the mixture was extracted twice with ethyl acetate. The aqueous layer was adjusted to pH 12 with K$_2$CO$_3$ and then extracted with methylene chloride. The solvent was dried over MgSO$_4$ and removed under vacuum to yield the crude product, which was then triturated with ether as ethanolic HCl was added. Repeated drying and washing with ether gave 0.118 g of title product. MS: 228 (M+H)$^+$. NMR (D$_2$O) δ: 2.01–2.24 (m, 2H), 2.34–2.43 (m, 1H), 3.02 (s, 3H), 3.27 (br s, 1H), 3.78 (br s, 1H), 3.92 (br s, 1H), 4.27 (dd, 1H, J=6, 11 Hz), 4.44 (dd, 1H, J=3, 11 Hz), 6.63–6.71 (m, 3H). Anal. Calcd for C$_{12}$H$_{16}$ClF$_2$NO.0.8 H$_2$O: C, 51.82; H, 6.38; N, 5.04; Found: C, 51.77; H, 6.06; N, 4.82.

EXAMPLE 9

2(R)-(3-Fluorophenoxymethyl)-pyrrolidine hydrochloride 9a. (R)-1-t-BOC-2-pyrrolidinemethanol Following the procedure of Example 1a, substituting N-t-BOC-D-proline for the N-t-BOC-L-proline thereof, the title compound was prepared.

9b. (R)-1-t-BOC-2-(3-fluorophenoxymethyl)-pyrrolidine

A complex (45 mmol) between TPP and TBAD in 100 mL of THF was prepared as described in Example 5b above. To this solution was added 6 g (29.85 mmol) of the (R)-1-t-BOC-2-pyrrolidinemethanol, from Example 9a above, and 5 g (38.5 mmol) of 3-fluorophenol (Aldrich). The reaction mixture was stirred at room temperature for 16 hr. The THF was removed by evaporation, and 15% HCl and methylene chloride were added. The aqueous layer was adjusted to approx. pH 12 with solid K$_2$CO$_3$, then extracted 3× with methylene chloride. The extracts were combined, dried and evaporated. The residue was dissolved in CHCl3, then triturated with ether and cooled. The crystals were filtered off, redissolved and chromatographed on silica gel. The product was obtained by removal of the solvent.

9c. (R)-2-(3-Fluorophenoxymethyl)-pyrrolidine hydrochloride

Following the procedures of Example 1c, adjusting the molar equivalents of the reagents appropriately, a 6.00 g (29.85 mmol) sample of (R)-1-BOC-2-(3-fluorophenoxymethyl)pyrrolidine, from step 9a above, was reacted, and 0.2 g of the title product was obtained. MS: 196 (M+H)$^+$, 213(M+NH$_4$)$^+$, 391 (2M+H)$^+$. NMR (D$_2$O) δ: 1.88–2.34 (m, 4H), 3.41 (t, 2H, J=7.4 Hz), 4.05–4.21 (m, 2H), 4.40 (dd, 1H, J=3, 10 Hz), 6.80–6.88 (m, 3H), 7.34–7.42 (m, 1H). Anal. Calcd for C$_{11}$H$_{14}$FNO.HCl: C, 57.02; H, 6.63; N, 6.05; Found: C, 56.66; H, 6.44; N, 5.99.

EXAMPLE 10

2(R)-(3-Fluorophenoxymethyl)-1-methylpyrrolidine hydrochloride

Following the procedures of Example 6, substituting (R)-1-methyl-2-pyrrolidinemethanol (Aldrich) for the (S)-1-methyl-2-pyrrolidinemethanol of Example 6, the title compound was prepared. MS: 210 (M+H)$^+$. NMR (CDCl$_3$) δ: 2.20–2.30 (m, 3H), 2.34–2.43 (m, 1H), 3.03 (s, 3H), 3.20–3.30 (m, 1H), 3.72–3.77 (m, 1H), 3.89–3.91 (m, 1H), 4.27 (dd, 1H, J=6, 11.5 Hz), 4.44 (dd, 1H, J=3, 11.5 Hz), 6.82–6.89 (m, 3H), 7.34–7.42 (m, 1H). Anal. Calcd for C$_{12}$H$_{17}$ClFNO.0.25 H$_2$O: C, 57.60; H, 7.05; N, 5.59; Found: C, 57.86; H, 6.76; N, 5.59.

EXAMPLE 11

2(S)-(2,3-Difluorophenoxymethyl)pyrrolidine hydrochloride 11a. 2(S)-(2,3-Difluorophenoxymethyl)pyrrolidine A 4.03 g (20 mmol) sample of (S)-1-t-butoxycarbonyl-2-pyrrolidinemethanol (from Example 3a above) and 3.90 g (30 mmol) of 2,3-difluorophenol (Aldrich) were added to a complex of TPP and TBAD, (prepared as in Example 5b above, 30 mmol of each) in 150 mL of THF. The reaction was stirred for 40 hr, and the solvents were removed under vacuum. Hexane was added to the residue, and the crude product was collected by filtration. The product was washed with hexane and 10% NaOH, then purified by flash chromatography on silica gel, eluting with CHCl$_3$. Removal of the solvent gave 7.5 g of the title compound.

11b. 2(S)-(2,3-Difluorophenoxymethyl)pyrrolidine hydrochloride

A 0.15 g sample of the compound from step 11a above was converted to the HCl salt by the procedure described in Example 1c. MS: 214 (M+H)$^+$, 231 (M+NH$_4$)$^+$. NMR (D$_2$O) δ: 1.89–2.35 (m, 4H), 3.43 (t, 2H, J=7.7 Hz), 4.10–4.18 (m, 1H), 4.27 (dd, 1H, J=8,10.7 Hz), 4.49 (dd, 1H, J=3, 10.7 Hz), 6.94–7.00 (m, 2H), 7.11–7.19 (m, 1H). Anal. Calcd for C$_{11}$H$_{14}$ClF$_2$NO: C, 52.91; H, 5.65; N, 5.61; Found: C, 52.96; H, 5.42; N, 5.65.

EXAMPLE 12

2(S)-(2,3-Difluorophenoxymethyl)-1-methylpyrrolidine hydrochloride

A 250 mg sample of 2(S)-(2,3-Difluorophenoxymethyl)pyrrolidine, from Example 11a above, was treated with formic acid and formaldehyde according to the procedure of Example 8 above to yield 110 mg of the title product. MS: 228 (M+H)$^+$. NMR (D$_2$O) δ: 2.03–2.27 (m, 3H), 2.35–2.45 (m, 1H), 3.06 (s, 3H), 3.28 (br s, 1H), 3.76 (br s, 1H), 3.95 (br s, 1H), 4.35 (dd, 1H, J=5, 11.5 Hz), 4.54 (dd, 1H, J= 3, 11.5 Hz), 6.94–7.03 (m, 2H), 7.11–7.20 (m, 1H). Anal. Calcd for C$_{12}$H$_{16}$ClF$_2$NO.0.4H$_2$O: C, 53.20; H, 6.25; N, 5.17; Found: C, 53.16; H, 6.12; N, 5.18.

EXAMPLE 13

2(S)-(3,4-Difluorophenoxymethyl)pyrrolidine hydrochloride 13a. (S)-1-t-Butoxycarbonyl-2-(3,4-difluorophenoxymethyl)-pyrrolidine A complex (30 mmol) between TPP and TBAD in 150 mL of THF was prepared as described in Example 5b above. To this solution was added 4.03 g (20 mmol) of the (S)-1-t-BOC-2-pyrrolidinemethanol, from Example 1a above, and 3.90 g (30 mmol) of 3-fluorophenol (Aldrich). The reaction mixture was stirred at room temperature for 40 hr. The THF was removed by evaporation, hexane was added and crystalline solid filtered off. The crude product was washed with 10% NaOH solution and chromatographed to yield 3.45 g of title compound.

13b. 2(S)-(3,4-Difluorophenoxymethyl)pyrrolidine hydrochloride

A 300 mg sample of the compound from step 13a above was treated according to the procedure of Example 1c to afford 145 mg of the title product. MS: 214 (M+H)$^+$, 231 (M+NH$_4$)$^+$. NMR (D$_2$O) δ: 1.87–2.11 (m, 1H), 2.04–2.18 (m, 2H), 2.20–2.33 (m, 1H), 3.41 (t, 2H, J=7.4 Hz), 4.03–4.17 (m, 2H), 4.36 (dd, 1H, J=3, 10 Hz), 6.77–6.83 (m, 1H), 6.97 (ddd, 1H, J=3, 6.6, 9.5 Hz), 7.25 (q, 1H, J= 9.2 Hz). Anal. Calcd for C$_{11}$H$_{14}$ClF$_2$NO: C, 52.91; H, 5.65; N, 5.61; Found: C, 52.61; H, 5.40; N, 5.60.

EXAMPLE 14

2(S)-(3,4-Difluorophenoxymethyl)-1-methylpyrrolidine hydrochloride

A 300 mg sample of (S)-1-t-Butoxycarbonyl-2-(3,4-difluorophenoxymethyl)pyrrolidine, from Example 13a above, was treated with formic acid and formaldehyde according to the procedure of Example 8 to afford 67 mg of the title product. MS: 228 (M+H)$^+$. NMR (D$_2$O) δ: 2.0–2.25 (m, 3H), 2.35–2.42 (m, 1H), 3.02 (s, 3H), 3.2–3.3 (br m, 1H), 3.7–3.8 (br s, 1H), 3.85–3.95 (br s, 1H), 4.24 (dd, 1H, J=6, 11.5 Hz), 4.42 (dd, 1H, J=3.3, 11.5 Hz), 6.78–6.84 (m, 1H), 6.95–7.02 (m, 1H), 7.2–7.3 (m, 1H). Anal. Calcd for C$_{12}$H$_{16}$ClF$_2$NO.1.85 H$_2$O: C, 48.52; H, 6.40; N, 4.72; Found: C, 48.50; H, 5.40; N, 4.07.

EXAMPLE 15

2(S)-(3-Chlorophenoxymethyl)-1-methylpyrrolidine hydrochloride 15a, 2(S)-(3-Chlorophenoxymethyl)-1-methylpyrrolidine A 2 g (17.4 mmol) sample of (S)-1-methyl-2-pyrrolidinemethanol (from Aldrich) and 2.8 g (22 mmol) of 3-chlorophenol (Aldrich) were added to a complex of TPP and TBAD, (prepared as in Example 5b above, 22 mmol of each) in 150 mL of THF. The reaction was stirred for 4 hr. The solvents were removed, the residue was stirred with 15% HCl, and the mixture was extracted with ether. The aqueous solution was then adjusted to pH 12 with K$_2$CO$_3$ and extracted with methylene chloride. The solvent was removed, and the residue was triturated with ether, the precipitate was removed by filtration, and the solvent was removed to give the crude product. The residue was purified by chromatography on silica gel.

15a. 2(S)-(3-Chlorophenoxymethyl)-1-methylpyrrolidine hydrochloride

The purified product from step 15a above was treated according to the procedure of Example 1c to afford 180 mg of the title product. MS: 226 (M+H)$^+$, 228 (M+H)$^+$. NMR (D$_2$O) δ: 2.01–2.24 (m, 3H), 2.34–2.43 (m, 1H), 3.03 (s, 3H), 3.10–3.30 (m, 1H), 3.75–3.90 (m, 1H), 3.95 (br, 1H), 4.27 (dd, 1H, J=6, 11.4), 4.45 (dd, 1H, J=3, 11.4), 6.97–7.02 (m, 1H), 7.11–7.13 (m, 2H), 7.33–7.39 (m, 1H). Anal. Calcd for C$_{12}$H$_{17}$Cl$_2$NO: C, 54.97; H, 6.54; N, 5.35; Found: C, 54.64; H, 6.38; N, 5.50.

EXAMPLE 16

2(S)-(3,4-Dichlorophenoxymethyl)-1-methylpyrrolidine hydrochloride 16a. 2(S)-(3,4-Dichlorophenoxymethyl)pyrrolidine A 1.84 g (16 mmol) sample of (S)-1-methyl-2-pyrrolidinemethanol (from Aldrich) and 3.91 g (24 mmol) of 3-chlorophenol (Aldrich) were added to a complex of TPP and TBAD, (prepared as in Example 5b above, 24 mmol of each) in 150 mL of THF. The reaction was stirred for 64 hr, then 20 mL of TFA were added and the reaction stirred for 1 hr. The solvents were removed, the residue was stirred with 15% HCl, and the mixture was extracted with ether. The aqueous solution was then adjusted to pH 12 with K$_2$CO$_3$ and extracted with methylene chloride. The solvent was removed, and the residue was triturated with ether, the precipitate was removed by filtration, and the solvent was removed to give the crude product. The residue was purified by chromatography on silica gel, eluting with 5% ethanol in CHCl$_3$.

16b, 2(S)-(3,4-Dichlorophenoxymethyl)-1-methylpyrrolidine hydrochloride

The purified product from step 16a above was treated according to the procedure of Example 1c to afford 55 mg of the title product. MS: 260 (M+H)$^+$, 262 (M+H)$^+$. NMR (D$_2$O) δ: 1.74–2.07 (m, 3H), 2.19–2.31 (m, 1H), 2.75 (b, 1H), 2.91 (s, 3H), 3.09–3.13 (b, 1H), 3.57 (b, 1H), 3.80 (b, 1H), 4.38 (b, 1H, under water peak), 7.05 (dd, 1H, J=3, 9 Hz), 7.35 (d, 1H, J=3 Hz), 7.58 (d, 1H, J=9 Hz), 10.6 (br, 1H). Anal. Calcd for C$_{12}$H$_{16}$Cl$_3$NO: C, 48.59; H, 5.44; N, 4.72; Found: C, 48.74; H, 5.47; N, 4.67.

EXAMPLE 17

(S)-2-(3-(acetamido)phenoxymethyl)pyrrolidine hydrochloride 17a. (S)-1-BOC-2-(3-(acetamido)phenoxymethyl)pyrrolidine A 1.5 g (7.46 mmol) sample of (S)-1-BOC-2-pyrrolidinemethanol (from Aldrich) and 1.69 g (11.19 mmol) of 3-acetamidophenol (Aldrich) were added to a complex of TPP and TBAD, (prepared as in Example 5b above, 11.19 mmol of each) in 50 mL of THF. The reaction was stirred for 16 hr, the solvents were removed under vacuum, and the residue was chromatographed on silica gel, eluting with 100:3 chloroform:methanol to give 1.62 g of the title compound.

17b. (S)-2-(3-(acetamido)phenoxymethyl)pyrrolidine hydrochloride

A 600 mg sample of the purified product from step 17a above was treated according to the procedure of Example 1c, extracting with chloroform instead of methylene chloride and eluting with 20:1 to 40:1 chloroform:methanol, to afford 325 mg of the title product. MS: 235 (M+H)$^+$. NMR (D$_2$O) δ: 1.8–23. (m, 5H), 3.41 (t, 1H, J=7 Hz), 4.05–4.20 (m, 2H), 4.40 (dd, 1H, J=3.3, 10.6 Hz), 6.88 (dd, 1H, J=2.5, 8 Hz), 7.02 (dd, 1H, J=1, 8 Hz), 7.20 (s, 1H), 7.38 (t, 1H, J=8 Hz). Anal. Calcd for C$_{13}$H$_{18}$N$_2$O$_2$.1.0 HCl.0.2 H$_2$O: C, 56.91; H, 7.13; N, 10.21; Found: C, 56.58; H, 6.91; N, 10.06.

EXAMPLE 18

(S)-2-(3-cyanophenoxymethyl)pyrrolidine hydrochloride 18a. (S)-1-BOC-2-(3-cyanophenoxymethyl)pyrrolidine A 1.5 g (20 mmol) sample of (S)-1-BOC-2-pyrrolidinemethanol (from Example 1a) and 3.57 g (30 mmol) of 3-cyanophenol (Aldrich) were added to a complex of TPP and DEAD, (prepared as in Example 5b above, 30 mmol of each) in 100 mL of THF. The reaction was stirred for 16 hr, the solvents were removed under vacuum, and the residue was extracted with hexane and chromatographed on silica gel, eluting with 100:0–85:15 hexane:ethyl acetate to give 2.71 g of the title compound. MS: 303 (M+H)$^+$, 320 (M+NH$_4$)$^+$. NMR (CDCl$_3$) δ: 1.48 (s, 9H), 1.84–2.05 (m, 4H), 3.35–3.45 (br, 2H), 3.75–3.95 (m, 1H), 4.05–4.18 (br, 2H), 7.25–7.40 (m, 4H).

18b. (S)-2-(3-cyanophenoxymethyl)pyrrolidine hydrochloride

A 1.3 g sample of the purified product from step 18a above was treated according to the procedure of Example 1c, eluting with 100:1 to 95:5 chloroform:methanol, to afford 486 mg of the title product. MS: 203 (M+H)$^+$, 220 (M+NH$_4$)$^+$. NMR (D$_2$O) δ: 1.9–2.35 (m, 4H), 3.43 (t, 2H, J=6 Hz), 4.07–4.16 (m, 1H), 4.20 (dd, 1H, J=8, 11 Hz), 4.44 (dd, 1H, J=3, 10 Hz), 7.33–7.56 (m, 4H). Anal. Calcd for $C_{12}H_{14}N_2O$: C, 60.38; H, 6.37; N, 11.73; Found: C, 60.31; H, 6.51; N, 11.45.

EXAMPLE 19

(S)-2-(3-cyanophenoxymethyl)-1-methylpyrrolidine hydrochloride

A 1.3 g sample of (S)-1-BOC-2-(3-cyanophenoxymethyl)pyrrolidine, from Example 19a above, was treated with formic acid and formaldehyde according to the procedure of Example 8 to afford 803 mg of the title product. MS: 217 (M+H)$^+$. NMR (D$_2$O) δ: 2.05–2.27 (m, 3H), 2.35–2.45 (m, 1H), 3.03 (s, 3H), 3.24–3.33 (m, 1H), 3.70–3.78 (m, 1H), 3.89–3.97 (m, 1H), 4.32 (dd, 1H, J=6, 11 Hz), 4.49 (dd, 1H, J=3, 11.5 Hz) 7.34–7.57 (m, 4H). Anal. Calcd for $C_{13}H_{16}N_2O$: C, 61.72; H, 6.72; N, 11.08; Found: C, 61.82; H, 7.00; N, 11.08.

EXAMPLE 20

1-methyl-2(S)-(phenoxymethyl)pyrrolidine hydrochloride 20a. (S)-1-BOC-2-(phenoxymethyl)pyrrolidine A 2.01 g (10 mmol) sample of (S)-1-BOC-2-pyrrolidinemethanol (from Example 1a) and 1.41 g (15 mmol) of phenol (Aldrich) were added to a complex of TPP and DEAD, (prepared as in Example 5b above, 15 mmol of each) in 100 mL of THF. The reaction was stirred for 16 hr, the solvents were removed under vacuum, and the residue was extracted with hexane and chromatographed on silica gel to give 0.7 g of the title compound.

20b. 1-methyl-2(S)-(phenoxymethyl)pyrrolidine hydrochloride

A 0.65 g sample of the purified product from step 20a above was treated according to the procedure of Example 1c, eluting with 100:2 to 100:4 chloroform:methanol, to afford 325 mg of the title product. MS: 192 (M+H)$^+$. NMR (D$_2$O) δ: 2.01–2.26 (m, 3H), 2.34–2.43 (m, 1H), 3.03 (s, 3H), 3.28 (br s, 1H), 3.28 (br s, 1H), 3.90 (br s, 1H), 4.27 (dd, 1H, J=6, 12 Hz), 4.45 (dd, 1H, J= 3.5, 11.5 Hz). Anal. Calcd for $C_{12}H_{17}N_2O \cdot HCl \cdot 0.25H_2O$: C, 62.06; H, 8.03; N, 6.03; Found: C, 61.81; H, 8.07; N, 5.94.

EXAMPLE 21

2(S)-(phenoxymethyl)pyrrolidine hydrochloride

A 0.21 g sample of (S)-1-BOC-2-phenoxymethyl)pyrrolidine, from Example 20a above, was treated with formic acid and formaldehyde according to the procedure of Example 8 to afford 125 mg of the title product. MS: 178 (M+H)$^+$, 195 (M+NH$_4$)$^+$. NMR (D$_2$O) δ: 1.88–2.34 (m, 4H), 3.44 (dt, 2H, J= 2.5, 7), 4.05–4.16 (m, 1H), 4.16 (dd, 1H, J=7.5, 11 hz), 4.41 (dd, 1H, J=3, 10.5 Hz), 7.03–7.13 (m, 3H), 7.38–7.45 (m, 2H).

EXAMPLE 22

2(S)-(3-(nitro)phenoxymethyl)azetidine methanesulfonate 22a. (S)-1-t-butoxycarbonyl-2-(3-(nitro)phenoxymethyl)azetidine A 2.25 g (1.2 mmol) sample of (R)-1-t-butoxycarbonyl-2-azetidinemethanol (prepared as in Example 1b above, except replacing the N-BOC-L-proline thereof with N-BOC-S-azetidinecarboxylic acid) and 2.25 g (18 mmol) of 3-nitrophenol (Aldrich) were added to a complex of TPP and DEAD (prepared as in Example 1 above, 18.1 mmol of each) in 80 mL of THF. The reaction was stirred for 16 hr, the solvents were removed under vacuum, and the residue was chromatographed on silica gel, eluting with a gradient of 1:1, 1:2, 1:3, 1:4 chloroform:hexane to give 1.5 g (40%) of the title compound.

22b. 2(S)-(3-(nitro)phenoxymethyl)azetidine methanesulfonate

A 278 mg sample of the purified product from step 22a above was treated according to the procedure of Example 1c (except starting with the methanesulfonic acid instead of HCl/ether) to afford 78 mg of the title product. MS: 209 (M+H)$^+$. NMR (D$_2$O) δ: 2.70 (q, 2H, J=8.1 Hz), 2.80(s, 3H), 4.08–4.18 (m, 2H), 4.46 (d, 2H, J=4.0 Hz), 4.90–4.96 (m, 1H), 7.45–7.49 (m, 1H), 7.60 (t, 1H, 8.4 Hz), 7.90 (t, 1H, 2.4), 7.93–7.96 (m, 1H). Anal. Calcd for $C_{10}H_{12}ClN_2O_3 \cdot 1.16 CH_3SO_3H$: C, 34.60; H, 5.21; N, 5.93; Found: C, 34.25; H, 5.25; N, 6.08.

EXAMPLE 23

(R)-1-methyl-2-(3-(nitro)phenoxymethyl)azetidine hydrochloride

A 200 mg (0.65 mmol) sample of (S)-1-t-butoxycarbonyl-2-(3 -(nitro)phenoxymethyl)-azetidine from Example 22a above, was treated with TFA/methylene chloride according the procedure 1c. The resultant crude product was then reacted with sodium cyanoborohydride (0.30 g) and formalin (2 mL) in ethanol (6 mL). After completion of the reaction, solvent was evaporated and the residue was dissolved in 1N KHSO$_4$. The aqueous solution was washed with ether, then adjusted to pH 12 with K$_2$CO$_3$ and extracted with chloroform. The solvent was dried over MgSO$_4$ and removed under vacuum to yield the crude product, which was then chromatographed on silica gel to give 83 mg. The title compound was then prepared according to the procedure described in Example 1c. MS: 223 (M+H)$^+$, 240 (M+NH$_4$)$^+$. NMR (D$_2$O) δ: 2.60–2.72 (m, 2H), 2.98 (s, 3H), 3.94–4.04 (m, 1H), 4.17–4.20 (m, 1H), 4.42–4.60 (m, 2H), 4.70–4.87 (m, 1H), 7.48 (m, 1H), 7.61 (t, 1H, J=8 Hz), 7.91 (t, 1H, J=2.2 Hz), 7.95 (m, 1H). Anal. Calcd for $C_{11}H_{15}ClN_2O_3$: C, 51.07; H, 5.84; N, 10.83; Found: C, 50.79; H, 5.89; N, 10.90.

The foregoing examples are merely illustrative of the invention and are not intended to limit the invention to the disclosed compounds. Variations and changes which are obvious to one skilled in the art are intended to be within the scope of the appended claims.

What is claimed is:

1. A method for treating dementias, attentional hyperactivity disorder, or substance abuse withdrawal characterized by decreased cholinergic function comprising administering to a patient in need of such treatment a therapeutically-effective amount of a compound of the formula:

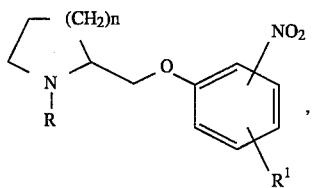

wherein n is 0 or 1, R is hydrogen or methyl, and $R^1$ is hydrogen or nitro; or a pharmaceutically-acceptable salt or prodrug thereof.

2. A method according to claim 1, wherein said compound is:

2(S)-(3-(nitro)phenoxymethyl)pyrrolidine;
1-methyl-2(S)-(3-(nitro)phenoxymethyl)pyrrolidine;
2(R)-(3-(nitro)phenoxymethyl)pyrrolidine;
1-methyl-2(R)-(3-(nitro)phenoxymethyl)pyrrolidine;
2(S)-(3-(nitro)phenoxymethyl)azetidine; or
1-methyl-2(R)-(3-(nitro)phenoxymethyl)azetidine.

3. A method for treating dementias, attentional hyperactivity disorder, or substance abuse withdrawal characterized by decreased cholinergic function comprising administering to a patient in need of such treatment a therapeutically-effective amount of a compound which is:

2(S)-(3-fluorophenoxymethyl)pyrrolidine;
2(S)-(3-fluorophenoxymethyl)-1-methyl-pyrrolidine;
2(S)-(3,5-difluorophenoxymethyl)pyrrolidine;
2(S)-(3,5-difluorophenoxymethyl)-1-methyl-pyrrolidine;
2(R)-(3-fluorophenoxymethyl)-pyrrolidine;
2(R)-(3-fluorophenoxymethyl)-1-methyl-pyrrolidine;
2(S)-(2,3-difluorophenoxymethyl)pyrrolidine;
2(S)-(2,3-difluorophenoxymethyl)-1-methylpyrrolidine;
2(S)-(3,4-difluorophenoxymethyl)pyrrolidine;
2(S)-(3,4-difluorophenoxymethyl)-1-methylpyrrolidine;
2(S)-(3-chlorophenoxymethyl)-1-methylpyrrolidine;
2(S)-(3,4-dichlorophenoxymethyl)-1-methylpyrrolidine;
2(S)-(3-(acetamido)phenoxymethyl)pyrrolidine;
2(S)-(3-cyanophenoxymethyl)pyrrolidine;
2(S)-(3-cyanophenoxymethyl)-1-methylpyrrolidine;
1-methyl-2(S)-(phenoxymethyl)pyrrolidine; or
2(S)-(phenoxymethyl)pyrrolidine.

* * * * *